(12) United States Patent
Warford, II et al.

(10) Patent No.: US 6,620,859 B2
(45) Date of Patent: Sep. 16, 2003

(54) METHODS OF PREPARING POLYMERIZABLE DENTAL COMPOSITIONS WITH IMPROVED TASTE OR AROMA, AND THAT PREVENT OXYGEN-INHIBITED LAYER

(75) Inventors: John H. Warford, II, Bismark, ND (US); John H. Warford, III, Bismark, ND (US); Edward C. Combe, Maplewood, MN (US)

(73) Assignee: Dakota Dental Development, Inc., Bismarck, ND (US)

( * ) Notice: Subject to any disclaimer, the term of this patent is extended or adjusted under 35 U.S.C. 154(b) by 0 days.

(21) Appl. No.: 09/738,080

(22) Filed: Dec. 15, 2000

(65) Prior Publication Data

US 2002/0077382 A1 Jun. 20, 2002

(51) Int. Cl.⁷ ............................. A61K 6/00; A61C 5/04
(52) U.S. Cl. ...................... 523/115; 523/116; 523/118; 523/120; 106/35; 433/226; 433/228.1
(58) Field of Search ................................. 424/439, 440, 424/464, 49; 428/372; 433/226, 212.1, 195; 427/495, 581, 2.3, 2.1; 528/274, 303; 106/35; 523/115, 116, 118, 120

(56) References Cited

U.S. PATENT DOCUMENTS

| | | | | |
|---|---|---|---|---|
| 3,819,568 A | * | 6/1974 | Taylor et al. ............ 260/42.52 |
| 3,943,949 A | | 3/1976 | Ashton et al. ................ 132/89 |
| 4,182,035 A | | 1/1980 | Yamauchi et al. .......... 433/228 |
| 4,222,780 A | | 9/1980 | Shibatani et al. ............. 106/35 |
| 4,235,633 A | | 11/1980 | Tomioka et al. .............. 105/35 |
| 4,259,075 A | | 3/1981 | Yamauchi et al. .......... 433/217 |
| 4,259,117 A | | 3/1981 | Yamauchi et al. ............ 106/35 |
| 4,374,822 A | | 2/1983 | Fine et al. .................... 424/49 |
| RE31,954 E | | 7/1985 | Fine et al. .................... 424/49 |
| 4,669,983 A | | 6/1987 | Bunker .................... 433/217.1 |
| 4,710,217 A | | 12/1987 | Bailey et al. .................. 65/31 |
| 4,738,722 A | | 4/1988 | Ibsen et al. ................... 106/35 |
| 4,758,163 A | | 7/1988 | Goldman .................... 433/229 |
| 4,773,933 A | | 9/1988 | Futami et al. ................ 106/35 |
| 4,968,725 A | | 11/1990 | Mukai et al. |
| 5,015,180 A | | 5/1991 | Randklev ....................... 433/9 |
| 5,051,130 A | | 9/1991 | Futami et al. ................ 106/35 |
| 5,063,257 A | | 11/1991 | Akahane et al. ............ 523/116 |
| 5,073,363 A | | 12/1991 | Pellico |
| 5,080,583 A | | 1/1992 | Hunting |
| 5,130,122 A | | 7/1992 | Tabibi et al. .................. 424/49 |
| 5,154,613 A | | 10/1992 | Cohen ...................... 433/228.1 |
| 5,177,121 A | | 1/1993 | Bunker ........................ 523/116 |
| 5,252,697 A | | 10/1993 | Jacobs et al. |
| 5,522,725 A | | 6/1996 | Jordan et al. ................... 433/9 |
| 5,554,030 A | | 9/1996 | Ario et al. ................... 433/226 |
| 5,575,645 A | | 11/1996 | Jacobs et al. ................... 433/9 |
| 5,595,487 A | | 1/1997 | Ario et al. ................... 433/226 |
| 5,621,119 A | * | 4/1997 | Podszun et al. ............. 549/229 |
| 5,639,239 A | | 6/1997 | Earle .......................... 433/218 |
| 5,645,429 A | | 7/1997 | Blackwell et al. ........ 433/217.1 |
| 5,662,886 A | | 9/1997 | Oxman et al. ................. 424/49 |
| 5,696,181 A | | 12/1997 | Chang et al. ................ 523/118 |
| 5,708,052 A | | 1/1998 | Fischer et al. |
| 5,711,665 A | | 1/1998 | Adam et al. .................... 433/9 |
| 5,756,559 A | | 5/1998 | Blackwell et al. ........... 523/115 |
| 5,766,012 A | * | 6/1998 | Rosenbaum et al. ...... 433/228.1 |
| 5,900,230 A | | 5/1999 | Cutler .......................... 424/49 |
| 5,932,627 A | | 8/1999 | Blackwell .................... 523/118 |
| 5,961,958 A | | 10/1999 | Homola et al. |
| 6,239,191 B1 | * | 5/2001 | Wong et al. |
| 6,423,762 B1 | * | 7/2002 | Wong et al. |

FOREIGN PATENT DOCUMENTS

| | | |
|---|---|---|
| DE | 197 22 596 | 12/1998 |
| EP | 0 674 896 | 10/1995 |
| GB | 948 204 | 1/1964 |
| WO | WO 99/07329 | 2/1999 |

OTHER PUBLICATIONS

Warford III, Combe, Warford II, U.S. patent application Publication 2001/0006623, appl. No. 09/427,876.*
O'Brien, "Dental Materials and Their Selection", Appendix A, p. 332, 1997.
Sano, et al., "Relationship between surface area for adhesion and tensile bond strength—Evaluation of a micro–tensile bond test," *Dental Materials*, Jul. 1994, pp. 236–240.

* cited by examiner

*Primary Examiner*—Tae H. Yoon
(74) *Attorney, Agent, or Firm*—Kagan Binder, PLLC

(57) ABSTRACT

Described are methods of improving cure of polymerizable dental materials by preventing oxygen inhibition; preferred embodiments relate to methods wherein the dental compositions comprises a polymerizable sealant and the barrier material comprises an essential oil.

37 Claims, No Drawings

METHODS OF PREPARING POLYMERIZABLE DENTAL COMPOSITIONS WITH IMPROVED TASTE OR AROMA, AND THAT PREVENT OXYGEN-INHIBITED LAYER

FIELD OF THE INVENTION

The invention relates to the field of polymerizable materials, specifically including polymerizable materials used in the practice of dentistry, such as sealants. According to the invention, a barrier material is used to mask flavor of the polymerizable material, and/or to impart flavor and aroma, and to prevent oxygen from being exposed to the polymerizable material during polymerization, thereby preventing oxygen from inhibiting polymerization of the material.

BACKGROUND

Polymerizable materials and related procedures are central ideas in dentistry. Polymerizable adhesives are used in orthodontic treatments to adhere brackets to tooth enamel. Polymerizable resin-based materials such as pit and fissure sealants are bonded to tooth enamel (e.g., a vital tooth, while the tooth is in the patient's mouth) to provide a coating that protects the enamel from decay. Adhesives may be used to secure a tooth filling material at its margins, to enamel and dentin, and reduce or eliminate the penetration of microbial agents across these margins. Adhesive materials may also be used to restore teeth in a number of ways. When a minor restoration or repair is required, e.g., as when a tooth is missing an incisal edge, a polymerizable material can be bonded to the surface of the tooth to replace the lost tooth matter. Adhesive materials are also used where a greater amount of oral rehabilitation is required, as in the cementing of inlays, crowns and bridges, and in aesthetic dentistry, where veneers can be cemented on an enamel facing of a tooth to mask a defect or discoloration.

Pit and fissure sealants are adhesive dental materials used to prevent tooth decay. Pits and fissures are sites on teeth that my be difficult to clean, with the risk of plaque stagnation and consequent possible onset of decay (caries). Pit and fissure caries may account for up to 90% of the total caries experience in some child populations (Combe, E C, Burke F J T & Douglas W H, 1999, Dental Biomaterials, p. 165 Boston: Kluwer Academic Publishers). Accordingly, the concept of sealing pits and fissures with resin applied to an etched enamel surface, known as fissure sealing, was developed in the 1960s, after the introduction of the acid-etch technique in 1955 (Buonocore M G, 1955, Journal of Dental Research, 34: 849–853). Such treatment is of benefit to patients at risk of occlusal caries, because the sealant will protect the susceptible pits and fissures from plaque accumulation and substrates that may be metabolized into destructive acids.

Of course, dental procedures benefit from patient comfort and patient cooperation during treatment. This can be difficult considering that many polymerizable materials that must be placed in the mouth, such as sealants, have a disagreeable taste or odor. There is always a need to improve comfort and cooperation of patients during treatment, for example by finding new ways of eliminating disagreeable tastes and odors of such materials. Also, it is necessarily a continuing goal to identify and use dental materials and procedures that are safe and biocompatible.

Adhesive materials such as sealants commonly include polymerizable dental materials that cure or harden by chemical polymerization reactions. Another problem with some such polymerizable materials is that their reactions can be inhibited by oxygen. Oxygen is known to react with free radicals of free-radically-polymerizable dental materials to give peroxide radicals of low reactivity, and which can unite to an oxygen-containing polymer (Combe E C, in Concise Encyclopedia of Medical and Dental Materials, Editor: Williams D, p. 10 Oxford: Pergamon Press). This inhibits polymerization.

A result of oxygen inhibition can be the formation of a layer at the surface of the polymerized dental material that is not fully polymerized (referred to as an "oxygen-inhibited layer" because oxygen has inhibited some of the desired polymerization reaction). The oxygen-inhibited layer, having not been completely reacted, contains unreacted or not-fully-reacted components.

In dentistry, an incompletely-polymerized surface of a dental material can have undesirable consequences. For example, the taste of unpolymerized materials can be objectionable, especially to children. Also, there can be health concerns, including the risk of patient exposure to unreacted chemicals of polymerizable dental materials. Some such chemicals can exhibit in-vitro cytotoxicity and allergenic potential. One chemical often used in dental sealants, bis-DMA (bisphenol A dimethacrylate), is said to react with salivary esterases to form bisphenol A, which is known to be an estrogen-mimicking agent (Rueggeberg, F A, Dlugokinski M & Ergle J W, 1999, Journal of the American Dental Association, 130: 1751–1757).

Dental practitioners have attempted to minimize exposure of patients to unreacted chemicals from dental sealants. See, e.g., Rueggeberg, F. A., D.D.S., et al., "Minimizing Patients' Exposure to Uncured Components in a Dental Sealant," JADA, Vol. 130, 1751 (December 1999). Rueggeberg et al, for example, found that treatments of cured dental materials with mechanical action and a mild abrasive yielded a reduction in uncured resin components.

There exists a need for methods of reducing dental patients' exposure to unreacted components of dental materials. Also, there is room for improving patient comfort and cooperation in dental procedures involving polymerizable dental materials.

SUMMARY

The invention relates to materials and methods involving polymerizable dental materials. The materials and methods can reduce or eliminate issues relating to the typically disagreeable taste of polymerizable dental materials. This is accomplished by the use of a barrier material preferably having desirable flavor and/or aroma, each of which can improve patient comfort and cooperation, with the aroma also having potential psychological benefits. The materials and methods also improve polymerization of the dental materials by preventing oxygen from inhibiting polymerization at the material surface. Improved polymerization provides the further benefits of reducing the amount of unpolymerized materials remaining in the mouth, which further eliminates disagreeable taste and also improves the strength of the polymerized material surface and simplifies procedures relating to application of the material in the mouth.

According to the invention, a barrier material is used to cover a polymerizable dental material placed in the mouth. Preferably, the barrier material can comprise an oil such as an essential oil. Preferred polymerizable dental materials include sealants, e.g., pit and fissure sealants. The barrier material covers up the taste of the polymerizable dental material and optionally provides its own desirable flavor and aroma, all of which add to patient comfort and cooperation during the procedure. At the same time, the barrier material prevents oxygen from reaching the polymerizable dental material where the oxygen would inhibit polymerization. This reduces the inhibitory effect that the oxygen would have on polymerization of the dental material and ultimately reduces the amount of unpolymerized material that will remain at the surface of the dental material, which can in turn reduce a patient's exposure to uncured materials.

An advantage of the invention is that the barrier material can be designed to allow for easy removal of the barrier material by rinsing, particularly if the barrier material contains an oil. Overall, the method is an improvement over past methods used for removing uncured polymerizable components from the mouth, such as by application of air or water from a syringe spray, the use of wet or dry cotton rolls, manual use of pumice with a cotton pellet, or the use of pumice in conjunction with a prophy cup in a dental handpiece. See generally, Rueggeberg et al.

The methods can be used to prevent oxygen inhibition of any polymerizable dental material, but can be specifically useful with oral adhesives and pit and fissure sealant.

An aspect of the invention relates to a method of applying a polymerizable dental sealant to a tooth. The method includes applying a barrier material to the sealant and polymerizing the sealant. Preferred barrier materials include an oil, e.g., an essential oil.

Another aspect of the invention relates to a method of applying a polymerizable dental material to a tooth. The method includes applying a barrier material comprising an essential oil to the polymerizable dental material, then polymerizing the polymerizable material.

Yet another aspect of the invention relates to a method of applying a polymerizable dental sealant to a tooth. The method includes preparing a tooth surface using an etchant, applying a polymerizable dental sealant to the etched surface, applying a barrier material to an exposed surface of the sealant, and polymerizing the sealant.

Yet another aspect of the invention relates to a method of preventing tooth decay. The method includes applying a polymerizable pit and fissure sealant to the tooth, applying a liquid barrier material to the sealant, the barrier material comprising an oil, and polymerizing the sealant.

Yet a further aspect of the invention relates to a method of curing a polymerizable dental material. The method includes reducing the amount of oxygen contacting the polymerizable dental material by providing a barrier material comprising an essential oil on the polymerizable dental material.

Yet a further aspect of the invention relates to a composition comprising a polymerizable dental material applied to a tooth, and a barrier material comprising an essential oil disposed on a surface of the polymerizable dental material.

DETAILED DESCRIPTION

Polymerizable dental materials include materials used to repair, replace, protect, or otherwise complement the surface of a tooth. Such materials include, for example, sealants, adhesives, composites, restoratives, and the like, which are well known in the dentistry arts.

The chemistry of the polymerizable dental material can be any chemistry, but the invention can be especially useful in combination with polymerizable dental materials whose cure can be inhibited by exposure to oxygen, especially free-radically polymerizable materials. Examples of such dental materials include materials commonly referred to as "resins," "resin composites," and "compomers."

Generally speaking, resins and resin composites are materials that typically cure or harden by free-radical addition polymerization activated by chemicals or more usually by radiation, commonly visible light. The term "resin" generally refers to the polymerizable component of a composition (alone or with other materials) while "resin composite" refers to the resin in combination with a filler material. Thus, resins and resin composites may contain inert inorganic fillers (silica, barium glass, zirconia/silica glass are some examples) to modify properties. These types of materials adhere micromechanically to tooth enamel, especially after acid etching, and bond to dentin via application of an acid conditioner followed by a primer and/or adhesive, after which a combination of micromechanical and interdiffusion bonding occurs. Many different types of resins and resin composites are commercially available, and typically vary in the type, concentration, and properties of the filler. Representative examples of commercially available resin composites include, but are not limited to, Revolution (Kerr Corporation, Orange, Calif.); Silux (3M, St Paul, Minn.); H R V Herculite (Kerr Corporation, Orange Calif.); Restorative Z100 (3M, St Paul, Minn.); and Alert (Pentron Inc, Wallingford, Conn.).

Glass ionomers may optionally be included in a polymerizable composition, in combination with a polymerizable resin. Glass ionomers, sometimes referred to as polyalkenoate cements, set and/or harden via an acid-base reaction wherein an acidic polymer or copolymer aqueous solution reacts with an ion-leachable glass. Glass ionomers are well known in the dental arts, and include, for example, poly (acrylic acid) and related copolymers which can react with a fluoroaluminosilicate glass (FAS) to give a product including a core containing unreacted FAS surrounded by the acid-base reaction products. Such materials are commercially available, for example from Ketac-Cem Radiopaque (Espe America, Inc, Norristown Pa.).

Polymerizable compositions that include a glass-ionomer are sometimes referred to as "resin-modified glass-ionomers" and can be used in situations where properties intermediate between those of resins and glass-ionomers are desired. Resin-modified glass-ionomers set and harden via a combination of an acid-base reaction and a free-radical polymerization reaction, which may be activated chemically and by radiation, e.g., visible light. Resin-modified glass-ionomers are well-known and commercially available. One representative example of a commercially available resin-modified glass-ionomer composition is GC Fuji II LC Improved (GC America Inc, Alsip, Ill.).

Compomers are another class of polymerizable dental materials that can be advantageously used where properties intermediate between those of resins or resin composites and glass-ionomers are desired. Compomers are polyacid-modified resin composites that polymerize via a free-radical polymerization mechanism. Compomers are well-known and commercially available. One example of a commercially available compomer includes is Compoglass® (Ivoclar North America Inc, Amherst, N.Y.).

The specific chemistry of the polymerizable dental material can preferably be any chemistry whose polymerization would be inhibited by oxygen. Many sealants include a mixture of monomers, usually including acrylates, e.g., di(meth)acrylates (as used herein, the term "(meth)acrylate" refers to both acrylates and methacrylates). Specific examples of dimethacrylates used in sealant formulations include Bis-GMA (Bisphenol A glycidyl methacrylate, often referred to as "Bowen's resin"), Bis-DMA, TEGDMA (triethylene glycol dimethacrylate), and UDMA (urethane dimethacrylate). Inert inorganic filler can be included to modify the appearance and/or mechanical properties of the sealant. Some products claim to contain fluoride-containing components.

Pit and fissure sealants may be classified according to their setting mechanism. According to standard specifications (ANSI/ADA Specification No. 39–1992; ISO 6874:1988; British Standard Specification BS 7180: 1989) there are two types of materials. Type 1 materials include a chemical setting mechanism, meaning that they contain a chemical activator. Type 2 materials are described as "external-energy-cured," meaning they cure upon application of an external source of energy such as visible light of an appropriate wavelength and intensity. Type 2 materials are often referred to as visible-light cure (VLC) materials. Both types of sealant set (i.e., polymerize) essentially by free-radical addition polymerization.

Examples of commercially available sealants include Concise™ White Sealant, available as Type 1 or a Type 2 material (3M Company, St. Paul, Minn.), FluoroShield™ (Type 2, Dentsply/Caulk, Milford, Del.), Helioseal® (Type 2, Ivoclar/Vivadent, Buffalo, N.Y.), Prisma-Shield® (Type 2, Dentsply/Caulk, Milford, Del.), Sealite™ (Type 2, Kerr USA, Romulus, Mich.) and Seal-Rite™ (Type 2, Pulpdent, Watertown, Mass.).

According to the invention, a barrier material is applied to the polymerizable dental material prior to polymerization, e.g., after the material has been placed in the mouth. The barrier material can cover or mask the taste of the polymerizable dental material. The barrier material can also impart its own desirable flavor and aroma into the process, allowing for improved patient comfort and cooperation; in this regard the barrier material can impart the flavor and odor of an essential oil and can optionally and preferably act as a vehicle for incorporating additional flavor or aroma such as by an added flavoring. Moreover, the barrier material can act as a barrier to prevent oxygen from contacting the polymerizable dental material, providing improved polymerization of the polymerizable material. As noted above, polymerization of polymerizable materials can be inhibited by oxygen. According to the invention, the barrier material is placed on a surface of the material to prevent oxygen from contacting the material where the oxygen would inhibit polymerization.

Because the barrier material is being used in dentistry environments, a number of features are important. The barrier material should be biocompatible, consisting of materials acceptable for oral use. When the barrier material is used with a radiation-curable dental material, the barrier material should be able to transmit such radiation. This is true, for example, when using the invention with Type 2 sealant materials where light must reach the sealant to activate polymerization. A barrier material should preferably form a continuous film over the polymerizable dental material. The barrier material should be chemically compatible with the polymerizable dental material and not cause chemical degradation. This of course will depend on the composition of the polymerizable dental material. The barrier material should be of a character that will at least cover up or mask a flavor of the polymerizable dental material, or ideally have a flavor and aroma that is tasteful. And, the barrier material should be convenient to apply to a tooth in a patient's mount.

The barrier material can preferably be a liquid comprising or based on an oil. Preferred oils include essential oils, for example soybean oil, safflower oil, sesame oil, olive oil, sunflower oil, canola oil, walnut oil, peanut oil, orange oil, eucalyptus oil, cod liver oil, castor oil, or a combination of two or more of these oils. Essential oils are suitable for use as a barrier material because many exhibit one or more properties including suitable flavor and/or liquidity for ease of application, chemical inertness, film-forming capability, and transparency to electromagnetic radiation. Also, essential oils are known to be compatible with resin based filling materials (see generally Applicants' U.S. patent application Ser. Nos. 09/427,876, 09/427,943, the disclosures of which are incorporated herein by reference).

An essential oil may be used by itself as the barrier material, a mixture of essential oils may be used, or an essential oil may be used with other ingredients (e.g., flavoring agents) included in amounts that do not unduly hinder the ability of the barrier material to cover a flavor or odor of the polymerizable dental material or to reduce the amount of oxygen reaching the polymerizable dental material.

Those with an understanding of polymerizable dental materials will understand that materials other than essential oils, for example other types of oils, may also be used in a barrier material, singly or in combination with essential oils or other materials. For example, liquids such as glycerol and propylene glycol can be used in combination with an essential oil. A flavor included in a barrier material may be any of a variety of desirable flavors, for example cherry, strawberry, blueberry, watermelon, lemon, lime, raspberry, apple, grape, cranberry, coconut, banana, tangerine, pineapple, bubble gum, almond, hazelnut, chocolate, etc.

The barrier material is applied to a surface of a polymerizable dental material, preferably by first placing the polymerizable dental material in the mouth, particularly at a tooth, and then applying the barrier material. Next, the polymerizable dental material can be polymerized. The polymerizable dental material is typically applied to a tooth after some preparation of the tooth, as is appropriate for the specific dental procedure and material being used. This can include cleaning and often some application of a primer or other treatment to promote adhesion. The polymerizable dental material is then applied to the prepared surface, as needed. Following placement of the polymerizable dental material, the barrier material is applied to the exposed surface of the dental material, and the dental material is then polymerized by appropriate means. The barrier material covers or masks the flavor of the dental material, and also reduces the amount of oxygen contacting the polymerizable dental material, preferably to entirely prevent environmental oxygen from contacting the dental material. The barrier material is applied to the polymerizable dental material in any fashion that will accomplish this, preferably in a fashion that will result in a continuous coating (e.g., a film) of barrier material over the surface of the polymerizable dental material. Examples of methods of applying the barrier material to a polymerizable composition include dropping, spreading, spraying, or brushing the barrier material onto the polymerizable dental material Specifically with respect to sealants, application of a sealant involves preparation of the tooth by first cleaning and drying a tooth surface. An etchant, usually based on phosphoric acid, is applied to the surface, e.g., a fissure, for typically 15 seconds, and the surface is washed to remove etching debris and thoroughly dried. The sealant is applied to the etched surface. According to the invention, a barrier material is applied to the exposed surface of the sealant, preferably in an amount and manner to form a continuous film over the sealant. The sealant is then polymerized. Optionally the barrier material can be washed away by rinsing with water.

EXAMPLE

A Type 2 fissure sealant (Helisoseal®, Ivoclar/Vivadent, Buffalo, N.Y.) was used in this study, tested by the method of Section 6.6 of ANSI/ADA Specification No. 39–1992). A drop of the sealant was placed on a microscope slide and covered with a glass cover slip to give an approximately round mass of sealant, with an edge of the material exposed to air and the two flat surfaces covered by glass. Polymerization was activated using a dental VLC unit (Caulk "The Max" Model 106, Caulk/Dentsply, Milford Del.) with output 470–480 nm wavelength and minimum intensity of 450 mW/square centimeter. The light was applied for 10 seconds. On examining the disc of material, visually, using a microscope, an oxygen inhibited zone was detected.

The above experiment was repeated, except that olive oil was placed on the drop of material before the application of the cover slip. When the cover slip was applied, the oil flowed and formed a barrier to air at the circumference of the material. Following polymerization as above, no oxygen inhibited zone could be detected microscopically.

What is claimed is:

1. A method of applying a polymerizable dental sealant to a tooth, the method including,
    applying a polymerizable dental sealant to a tooth,
    applying a barrier material to the sealant, wherein the barrier material comprises an oil that masks a flavor of the polymerizable dental sealant, and
    polymerizing the sealant.

2. The method of claim 1 wherein the barrier material provides an oxygen barrier to prevent oxygen from contacting the polymerizable dental sealant, to prevent the oxygen from inhibiting polymerization of the polymerizable dental sealant.

3. The method of claim 1 wherein the barrier material comprises an essential oil.

4. The method of claim 3 wherein the essential oil is selected from the group consisting of soybean oil, safflower oil, sesame oil, olive oil, sunflower oil, canola oil, walnut oil, peanut oil, orange oil, eucalyptus oil, cod liver oil, castor oil, and a combination of two or more of these oils.

5. The method of claim 1 wherein the barrier material comprises a flavoring.

6. The method of claim 1 wherein the polymerizable dental sealant is free-radically polymerizable.

7. The method of claim 1 wherein the polymerizable dental sealant comprises a resin, a resin composite, a compomer, or a mixture thereof.

8. The method of claim 1 wherein the method comprises applying a liquid barrier material to the sealant by dropping, spreading, spraying, or brushing the liquid barrier material onto the sealant.

9. A method of applying a polymerizable dental material to a tooth, the method including,
    applying a polymerizable dental material to a tooth,
    applying a barrier material comprising an essential oil to the polymerizable dental material, then
    polymerizing the polymerizable material.

10. The method of claim 9 wherein the barrier material masks a flavor of the polymerizable dental material.

11. The method of claim 9 wherein the barrier material provides an oxygen barrier to prevent oxygen from contacting the polymerizable dental material, to prevent the oxygen from inhibiting polymerization of the polymerizable dental material.

12. The method of claim 9 wherein the essential oil is selected from the group consisting of soybean oil, safflower oil, sesame oil, olive oil, sunflower oil, canola oil, walnut oil, peanut oil, orange oil, eucalyptus oil, cod liver oil, castor oil, and a combination of two or more of these oils.

13. The method of claim 9 wherein the barrier material further comprises a flavoring.

14. The method of claim 9 wherein the polymerizable dental material is free-radically polymerizable.

15. The method of claim 9 wherein the polymerizable dental material comprises a resin, a resin composite, a compomer, a glass ionomer, or a mixture thereof.

16. The method of claim 9 wherein the method comprises applying a liquid barrier material to the polymerizable dental material by dropping, spreading, spraying, or brushing the liquid barrier material onto the polymerizable dental material.

17. A method of applying a polymerizable dental sealant to a tooth, the method comprising
    preparing a tooth surface using an etchant,
    applying a polymerizable dental sealant to the etched surface,
    applying a barrier material to an exposed surface of the sealant, wherein the barrier material comprises an oil, and
    polymerizing the sealant.

18. The method of claim 17 wherein the sealant is applied to a fissure.

19. A method of preventing tooth decay by applying to a tooth a pit and fissure sealant, the method comprising
    applying a polymerizable pit and fissure sealant to the tooth,
    applying a liquid barrier material to the sealant, the barrier material comprising an oil,
    polymerizing the sealant.

20. The method of claim 19 further comprising rinsing the barrier material from the tooth.

21. The method of claim 19 wherein the oil comprises an essential oil.

22. A method of curing a polymerizable dental material, the method comprising reducing the amount of oxygen contacting the polymerizable dental material by providing a barrier material comprising an essential oil on the polymerizable dental material.

23. The method of claim 22 wherein polymerization of the polymerizable dental material is inhibited by oxygen.

24. The method of claim 22 wherein the method prevents the formation of an oxygen-inhibited layer in the polymerizable dental material.

25. A composition comprising a polymerizable dental material applied to a tooth, and an oxygen barrier material comprising an essential oil disposed on a surface of the polymerizable dental material.

26. The composition of claim 25 wherein the polymerizable dental material is a sealant.

27. A method of applying a polymerizable dental sealant to a tooth, the method including,
    applying a polymerizable dental sealant to a tooth,
    applying a barrier material to the sealant, wherein the barrier material comprises an oil, and
    polymerizing the sealant.

28. The method of claim 27 wherein the oil comprises an essential oil.

29. The method of claim 28 wherein the essential oil is chosen from the group consisting of soybean oil, safflower oil, sesame oil, olive oil, sunflower oil, canola oil, walnut oil, peanut oil, orange oil, eucalyptus oil, cod liver oil, castor oil, and a combination of two or more of these oils.

30. A method of applying a polymerizable dental sealant to a tooth, the method including, applying a polymerizable dental sealant to a tooth, applying a barrier material to the sealant, wherein the barrier material comprises a flavoring, and polymerizing the sealant.

31. A method of applying a polymerizable dental sealant to a tooth, the method including, applying a polymerizable dental sealant to a tooth, applying a liquid barrier material to the sealant by dropping, spreading, spraying, or brushing the liquid baffler material onto the sealant, and polymerizing the sealant.

32. A method of applying a polymerizable dental material to a tooth, the method including, applying a polymerizable dental material to a tooth, applying a barrier material comprising an oil to a polymerizable dental material, and polymerizing the polymerizable dental material.

33. The method of claim 32 wherein the barrier material masks a flavor of the polymerizable dental material.

34. The method of claim 32 wherein the barrier material comprises a flavoring.

35. A method of curing a polymerizable dental material, the method comprising:

providing polymerizable dental material that is inhibited by oxygen;

reducing the amount of oxygen contacting the polymerizable dental material by providing a barrier material on the polymerizable dental material, wherein the barrier material consists essentially of an essential oil or a mixture of essential oils, optionally, in combination with a flavoring; and preventing the formation of an oxygen-inhibited layer in the polymerizable dental material.

36. The method of claim 30, wherein the barrier material masks a flavor of the polymerizable dental sealant.

37. The method of claim 31, wherein the barrier material masks a flavor of the polymerizable dental sealant.

* * * * *